(12) United States Patent
Solosko et al.

(10) Patent No.: US 6,874,621 B2
(45) Date of Patent: Apr. 5, 2005

(54) METHOD AND PACKAGE FOR INCREASING ELECTRODE SHELF LIFE

(75) Inventors: Thomas A Solosko, Issaquah, WA (US); Anthony G. Picardo, Tacoma, WA (US); Steven Thomas Mydynski, Clinton, WA (US); Kim J. Hansen, Renton, WA (US); Seiya Ohta, Newcastle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/793,091

(22) Filed: Feb. 27, 2001

(65) Prior Publication Data

US 2002/0117408 A1 Aug. 29, 2002

(51) Int. Cl.[7] .............................................. B65D 81/24
(52) U.S. Cl. ...................................... 206/210; 206/701
(58) Field of Search ................................. 206/205, 210, 206/213.1, 438, 440, 701; 600/392, 394, 397; 53/403, 407, 431, 450, 467, 473

(56) References Cited

U.S. PATENT DOCUMENTS

| | | | | |
|---|---|---|---|---|
| 4,034,854 A | * | 7/1977 | Bevilacqua | .................. 206/438 |
| 4,353,373 A | * | 10/1982 | Sessions et al. | ............. 600/392 |
| 5,579,919 A | * | 12/1996 | Gilman et al. | ............... 206/438 |
| 5,850,920 A | | 12/1998 | Gilman et al. | |
| 5,938,012 A | * | 8/1999 | Yeager et al. | ................ 206/205 |
| 5,969,223 A | * | 10/1999 | Nagai et al. | .............. 206/213.1 |
| 6,119,855 A | * | 9/2000 | Yeager et al. | ............. 206/213.1 |

* cited by examiner

Primary Examiner—Luan K. Bui
(74) Attorney, Agent, or Firm—Tony Piotrowski (57) ABSTRACT

A package for increasing shelf life of electrodes packaged therein. A first package within which one or more gel-containing electrode pads are sealed. In addition, at least one moisture source is sealed within the package.

59 Claims, 7 Drawing Sheets

METHOD AND PACKAGE FOR INCREASING ELECTRODE SHELF LIFE

BACKGROUND OF THE INVENTION

1. Field of the Invention

The present invention relates to a sealed package for extending the shelf life of electrodes sealed within the package. Also, the present invention relates to a method for extending the shelf life of electrodes sealed within a package. Furthermore, the present invention relates to a release liner for covering an electrode pad.

2. Description of the Prior Art

Since packaged articles may remain in their packages for extended periods of time, it is often desired to control the conditions within a package. For example, humidity and temperature affect the condition of many packaged articles. Along these lines, packaged articles may require low humidity to help prevent damage or affect functioning. Inclusion of packets of silica gel, which absorb moisture, in many packages evidence the desire to control humidity in packages. The silica gel in a package can help to preserve the articles in a package in a desired state. Along these lines, silica gel absorbs moisture to maintain a dry environment. In other cases, it may be desired to maintain a moister environment in a package.

Sometimes, articles may be required to remain within a certain range in order to maintain a desired state or functionality. One example of such an article is electrode pads for medical uses. For example, electrode pads may include a hydrogel that facilitates their operation. The shelf life of electrode pads is determined in part by the length of time it takes for enough water moisture to evaporate out of the hydrogel and escape the pads package. As moisture escapes, the electrical properties of the electrode pads become increasingly compromised.

In one context, where electrode pads are utilized with a defibrillator, a very significant factor includes changes in small and large signal impedance values between a patient and a defibrillator. As the hydrogel dries out, the impedance values increase, making it more difficult to monitor a patient's electrical signals, obtain transthoracic impedance, and deliver energy into the body.

Water loss can affect the mechanical properties of the hydrogel as well. In some hydrogels, the loss of water causes the hydrogel to skin over or solidify, especially around the edges, which inhibits the ability of the hydrogel to adhere to the skin. This partial or complete loss of adhesion can render an electrode useless since it cannot then create or maintain an effective contact with the patient's skin. Thus, water loss from the electrode pad can prevent or attenuate receipt of electrocardiogram (ECG) signals by a defibrillator. In addition, water loss from the electrode pad can alter the delivery of defibrillation energy from a defibrillator to the patient.

Additionally, poor or uneven contact of the electrode pad with a patient's skin may unduly concentrate energy transfer during defibrillation into areas that exhibit good skin contact. Higher than usual current densities that result from poor or uneven skin contact can cause skin burns. If the current is not delivered to a patient in the manner that an electrode pad was designed for, the resulting treatment delivered to the patient may be altered, compromising patient outcome.

To help ensure that electrode pads will be usable when opened, electrode manufacturers currently print an expiration date on each set of pads. The electrode pads are to be discarded no later than the expiration date. However, the expiration date typically is determined based upon studies of the hydrogel used on the pads, and the amount of water moisture that escapes the package over time under normal as well as strenuous conditions. A safety factor is added to give time for the electrode pads to be shipped from the supplier to an original equipment manufacturer (OEM), and then from the OEM to the customer. This helps to ensure that the electrode pads are always usable, barring any package damage, when removed from the package before the expiration date.

Calculating the expiration date of electrode pads or other components as described above is a conservative method of ensuring quality. However, as a result, the expiration date may arrive before the pads have actually expired. In fact, electrode pads may be usable for much longer than the expiration date, especially if they are kept at room temperature or in a high humidity environment.

The above example only represents one particular example of an electrode pad of a particular use. Electrode pads for other uses may be similarly affected. Also, devices other than electrode pads may be affected by age and package conditions. Furthermore, factors other than humidity, such as corrosion or contaminants, can affect the functionality or shelf life of a device.

SUMMARY OF THE INVENTION

The present invention addresses problems related to ensuring operability of packaged devices. The present invention may be useful with a variety of products affected by a variety of conditions in their package. One advantage of the present invention is that it can extend the shelf life of electrodes or other humidity-dependent devices.

The present invention includes a package for increasing shelf life of electrodes packaged therein. The package includes a first package within which one or more electrodes are sealed. The electrodes include at least an electrode pad gel. The invention also includes at least one moisture source sealed within the package.

Also, the present invention includes a release liner for covering an electrode pad gel. The release liner includes metal foil.

Additionally, the present invention includes sealing the first package of electrodes, with or without the at least one moisture source, within a second package.

Furthermore, the present invention concerns a method for increasing shelf life of electrodes that include one or more gel-containing electrode pads. The method includes sealing at least one moisture source within a package with the one or more electrodes.

Still further, the present invention provides a method for increasing shelf life of electrodes including at least a gel-containing electrode pad. The method includes covering the electrode pads with a release liner comprising metal foil.

Further, the present invention provides a method for increasing shelf life of electrodes including sealing the first package of electrodes, with or without the at least one moisture source, within a second package.

Still other objects and advantages of the present invention will become readily apparent by those skilled in the art from a review of the following detailed description. The detailed description shows and describes preferred embodiments of the invention, simply by way of illustration of the best mode contemplated of carrying out the present invention. As will be realized, the invention is capable of other and different embodiments and its several details are capable of modifications in various obvious respects, without departing from the invention. Accordingly, the drawings and description are illustrative in nature and not restrictive.

BRIEF DESCRIPTION OF THE DRAWINGS

Objects and advantages of the present invention will be more clearly understood when considered in conjunction with the accompanying drawings, in which.

DESCRIPTION OF THE PREFERRED EMBODIMENTS

The present invention addresses, among others, problems associated with drying out of hydrogel on electrode pads. Although gel-containing electrode pads are discussed in particular, the present invention can find applicability to any packaged humidity sensitive article. The present invention relates to structures and methods for helping to prevent drying out of electrode pads.

The shelf life of electrode pads is determined in part by the rate of evaporation of moisture from gel in the pads and, therefore, the length of time that it takes for a particular amount of moisture to evaporate from the gel and escape from the pad's package. As discussed above, at a certain point, the level of moisture in the pads reaches a level where the pads do not function properly or at all. At this point, use of the pads with a defibrillator, for example, will be ineffective in treating a patient. Even before surpassing a critical level, electrical properties of the gel and, hence, the pads can deteriorate. Among the electrical properties that can be affected are the small and large signal impedances. As the gel dries out, impedance values increase, making it more difficult to monitor a patient's electrical signals, obtain transthoracic impedance, and deliver energy into the body.

While specific reference is made above to defibrillators, electrode pads are also useful with other treatment devices and monitoring devices. Drying out of electrode pads in any treatment or monitoring device can compromise patient treatment by providing erroneous data and/or ineffective treatment.

Moisture loss from electrode pads can also affect mechanical properties of the gel. In some gels, loss of water can cause a skin to form over the gel and/or cause the gel to solidify, particularly around the edges of the gel. Skinning over and solidification can affect the adhesion of the gel. As adhesion is reduced or eliminated, the electrode can rendered less effective or useless. With reduced or lack of adhesion, the electrode pad cannot maintain effective contact with a patient's skin. Partial skin contact can increase current densities in the contact area during defibrillation, for example. This can cause skin burns.

Reduced or eliminated adhesion can also make the pad less likely to remain on the skin. Elimination of contact will effectively create an open circuit. With loss of contact, no signals can pass between the body and an instrument that the electrodes are connected to. Also, energy cannot be delivered to a patient when needed with the pads in this condition.

Currently, to maintain the electrical and mechanical properties of electrodes and to increase electrode shelf life, electrode pads are packaged in metal foil pouches. Metal foil pouches provide excellent moisture vapor barriers that permit very little if any moisture to escape. However, metal foil pouch packaging limits electrode packaging options, especially when preconnected electrodes are desired. In such packages, metal foil pouches require a lead wire extending through the pouch. When the pouch is sealed to the lead wires, it is sometimes difficult to peel it completely off. As a result, the package stays on the lead wires after the electrodes are removed. This package can get in the way of the user. In addition, with the package sealed around the lead wires, there is a potential for moisture leaking between the leadwires and the package. Other packaging options can compensate for these difficulties, but may not provide a similar level of moisture vapor barrier. With a reduced moisture vapor barrier, moisture can escape from a package more quickly, causing the hydrogels in the electrode pads to dry out faster. This will shorten the shelf life of the electrodes.

The present invention addresses the problem of electrode shelf life by providing at least one additional moisture source within a package. By providing a source of moisture in addition to the hydrogel of the electrode pads, the present invention can reduce moisture loss from the gel of the electrode pads. Moisture in the gel of the electrode pads will escape to the environment within the electrode packaging. By introducing another moisture source in the packaging, with the moisture added from the second source will slow the rate of moisture loss from the electrode pad gel.

A package according to the present invention can include any typical electrode package or any other suitable material. Along these lines, the package could include a metal foil. The foil could be in the form of a pouch. The package could also include one or more formed plastic and/or foil members. Two formed members could be joined to make the package. Alternatively, a formed member could be covered with a plastic and/or foil member. The covering member could be in the form of a peelable cover. The package could also include a sealed cartridge.

According to one embodiment, an electrode is sealed within a first package that is in turn sealed within a second package. This could further reduce moisture loss. The first and/or the second package could be as described above. According to one embodiment, the second package could be another metal foil pouch.

Regardless of the construction of the package, the electrode leads could be packaged within the package. According to some embodiments, the leads are packaged within the package and are accessible from outside the package. This could permit testing of the electrodes while still packaged or access for any other purpose.

In a sense, electrode package interior can be viewed as a system in equilibrium. Along these lines, a certain amount of moisture is lost from the electrode package to the surrounding environment, regardless of the contents of the package. As moisture is lost from the package, moisture is lost from the electrode pads to replace the lost moisture. Without an additional source of moisture, one hundred percent of the moisture in the interior of the package and lost from the package will come from the electrode pads. The added moisture source adds moisture to the package interior, thus slowing the loss of moisture from the electrode pad gel. The electrode pads and the extra moisture source share the burden of adding moisture to the package interior. The gel and the additional moisture source will each lose less water over a given period of time, although the moisture loss from the package may and most likely will remain the same. As a result of introducing the additional moisture source, electrode shelf life will increase since the electrode pads will lose less water over a given period of time.

The present invention may utilize any number of additional moisture sources. For example, the additional moisture source may include one or more portions of gel, known as sacrificial gel. The gel may be similar to the gel in the electrode pads. The gel may have the same composition as the gel utilized in the electrode pads. Other moisture sources can include glycerin, glycerin-containing gels, plant resins, plant resin-containing gels, polymers, polymer-containing gels, alcohol, alcohol-containing gels, and/or any liquid or gel containing any other liquid.

According to one embodiment, the sacrificial gel not only has the same composition as the gel in the electrode pads, but the sacrificial gel is taken from the same batch of gel as the gel of the electrode pads. By formulating one batch of gel for making the electrode pads and the sacrificial gel, it can be ensured that all of the gel will have a similar chemical composition, including water content. This is one way for helping to ensure that the amount of moisture released by the electrode pad gel and the sacrificial gel is similar. By having the moisture loss rates similar, the present invention can help to ensure that the electrode pad gel moisture rate will be reduced.

Similar moisture loss rates will also help to ensure that the sacrificial gel will not loose moisture at a greater rate than the electrode pad gel, which could produce a moisture level in the package high enough for the electrode pad gel to absorb moisture. Just as with moisture loss, too much moisture gain can render the electrode pads inoperable by swelling the electrode pads and causing the electrode pads to loose their adhesive properties. On the other hand, if the moisture loss rate from the sacrificial gel were lower than the loss rate from the electrode pad gel, the electrode gel could lose moisture at a more rapid rate to feed the drier sacrificial gel.

While the sacrificial gel could have the same moisture content as the electrode pad gel, the gels could have different compositions. The moisture loss from the sacrificial gel, or any other moisture source, could be such that the sacrificial gel or other moisture source and the electrode pad gel emit moisture to the package at the same rate. The rate that the sacrificial gel emits moisture to the package could be controlled by at least partially covering the sacrificial gel with a cover. While no cover could be arranged on the sacrificial gel, the sacrificial gel could be entirely covered.

The sacrificial gel cover could at least partially transmit moisture. Controlling the amount of the sacrificial gel that is covered and the moisture permeability of any sacrificial gel cover can control moisture loss from the sacrificial gel. Also, controlling the exposed surface area of the sacrificial gel can control moisture loss from the sacrificial gel, whether or not a cover covers any of the exposed area.

One factor that may be considered in determining the desired moisture loss from the sacrificial gel or other moisture source is moisture loss from the electrode pad gel. Among the factors that can effect moisture loss from the electrode pad gel are the area of the electrode pad gel that is exposed. Typically, a release liner covers an electrode pad gel. The release liner covers the electrode pad gel except around the edges of the electrode pad gel. The release liner can be partially permeable to moisture or not at all. As a result, the release liner can affect the amount of moisture loss from the electrode pad gel. Therefore, the presence and characteristics of any release liner can affect the desired amount of moisture loss from the sacrificial gel or other moisture source.

Additionally, the number of electrodes and associated pads can affect the desired moisture loss from the sacrificial gel or other moisture source. For example, if a package includes two electrodes, each including a pad with gel, a greater degree of moisture loss from the sacrificial gel or other moisture source would be desired as compared to a package containing only one electrode. Along these lines, if the sacrificial gel or other moisture source has characteristics such that it emits a similar amount of moisture to the package interior as the electrode pad gel, if two electrodes were in the package, the moisture release from the sacrificial gel or other moisture source could be inadequate to extend the electrode shelf life a desired degree. In this case, the electrode gels would contribute more moisture to the inside of the package than the sacrificial gel or other moisture source. The sacrificial gel or other moisture source would need to be modified to accommodate for the greater moisture loss from the two electrode pads. For example, a greater portion of the surface area of a sacrificial gel could be exposed.

According to one example, the combined exposed edges of the electrodes is about one square inch, and the package containing the electrodes also contains one moisture source that includes a sacrificial gel similar to the electrode pad gel that has a similar exposed surface area. The remaining portion of the sacrificial gel is covered with a liner that transmits twice as much moisture as the release liner on the electrode pads. Since the package contains two electrode pads, the combined moisture released from the electrode pads will be similar to the moisture vapor transmission through the liner of the sacrificial gel. According to an alternative of this embodiment, another portion of sacrificial gel could be enclosed within the package to account for the increased moisture released from two or more as opposed to one electrode in the package.

Other sources of moisture could also be utilized according to the present invention. For example, a liquid could be sealed within the package. The above discussion with respect to moisture release rates from the sacrificial gel apples to a liquid moisture source as well.

One example of a liquid is water. An amount of liquid could be contained within a reservoir in the package. The reservoir could be built into a package wall. Alternatively, the liquid could be contained in a packet, similar to silica gel, sealed within the package. However the liquid is packaged, it should result in the desired moisture release rate.

Other sources of moisture can include a moisture-absorbing element. The moisture-absorbing element could be sealed within the package as the sacrificial gel. As with a liquid moisture source, the above discussion with respect to moisture release rates from the sacrificial gel applies to an absorbent element moisture source. Along these lines, the absorbent element moisture source could be at least partially covered with a moisture permeable cover or other type of cover. Examples of a moisture-absorbing element can include a sponge, a woven or non-woven material.

As referred to above, the electrode pad gel may be covered with a release liner. The presence of a release liner can also improve electrode shelf life by reducing moisture loss from the electrode pad gel. Regardless of whether the electrode package includes an additional source(s) of moisture, the electrodes may include a release liner. Similarly, a package may include an additional moisture source(s) even if a release liner does not cover the electrode pad gel. The release liner can include a metal foil, polymeric material, and any other suitable material. One embodiment simply includes a foil layer on the electrode gel.

A release liner can include multiple layers. The layers can include any polymeric, foil, or other materials. According to one embodiment, the release liner includes a polymeric layer adjacent to the electrode pad gel. A layer of metal foil is arranged on the polymeric layer. Another polymeric layer is arranged on the metal foil. The outer polymer layer can help to protect the underlying metal foil as well as to help seal any holes in the foil. The layers may have any suitable thickness.

The polymeric layers can include any suitable polymers. Along these lines, the polymeric layer could include polyethylene and/or polypropylene. If a polymer layer includes polyethylene, the polyethylene could be high or low density. If the release liner includes more than one polymer layer, each polymer layer could be different. A lower polymer layer can have a thickness of about 0.002 inch to about is 0.005 inch. An upper or outer polymer layer can have a thickness of about 0.002 inch to about 0.005 inch. These are typical release liner thickness. However, release liners can be as thick and/or rigid as desired.

As with any polymer layers, the foil layer could include any suitable metal foil. Along these lines, the foil could be aluminum. The foil layer can have a thickness of about 0.00035 inch to about 0.0007 inch. According to one particular embodiment, the foil has a thickness of about 0.00035-inch.

Regardless of the composition of the release liner, the release liner may include a low force release surface. The low force release surface may include any suitable material. According to one embodiment, the low force release surface includes silicone.

FIGS. 1–9 illustrate a few specific embodiments of the present invention. For example, FIGS. 1a, 1b, 1c illustrate an embodiment of the present invention that includes two electrode pads 3 and 5 on a release liner 1. The electrode pads are shown in FIG. 1a with the side opposite the gel in view. A lead 7 and 9 extends away from each electrode pad. A sacrificial gel portion 11 is also arranged on the release liner. The sacrificial gel portion in the embodiment shown in FIG. 1a has an area substantially similar to the area of each electrode pad. A cover on the sacrificial gel emits moisture at a rate twice that of the release liners on the electrode pads to account for the fact that the package contains two electrodes and only one sacrificial gel portion.

Figure 1A:
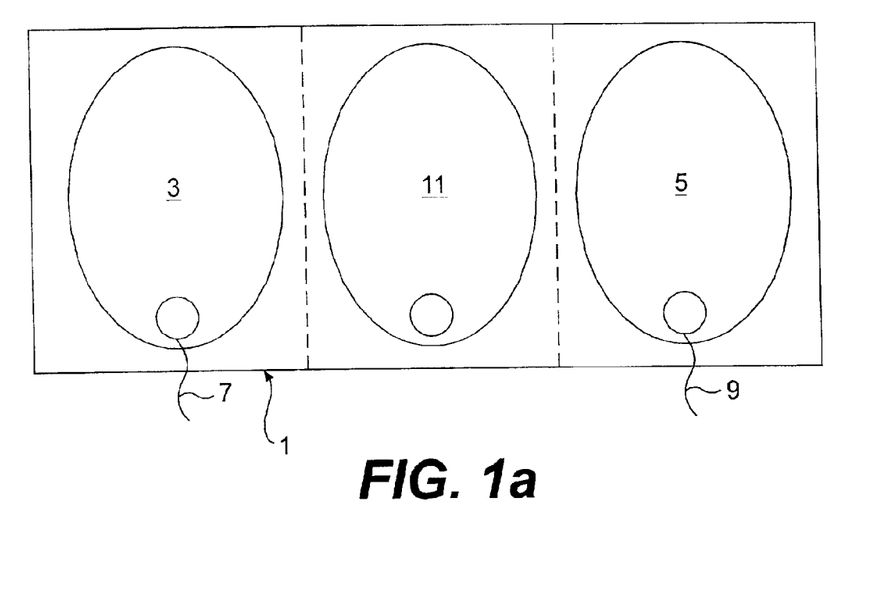
FIGS. 1a, 1b, 1c represent, respectively, an overhead and two perspective views of an embodiment of a set of electrodes according to the present invention that includes a sacrificial gel portion or other moisture source on the release liner with the electrode pads.
Figure 1B:
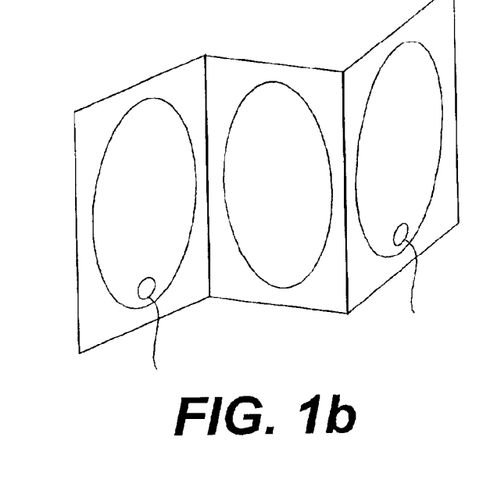
Figure 1C:
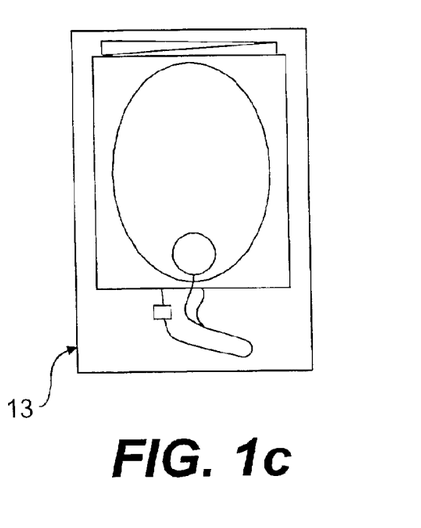

FIG. 1b illustrates the release liner in a partially folded position. Additionally, FIG. 1c shows the release liner and attached electrodes and sacrificial gel portion completely folded and contained within a package 13. The package could be a metal foil pouch or other material having a low moisture vapor transmission rate (MVTR).

Figure 2:
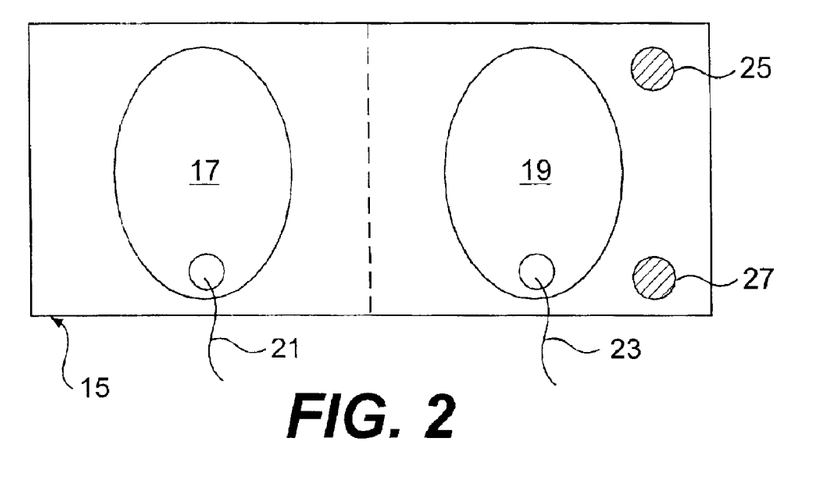
FIG. 2 represents an overhead view of another embodiment of a set of electrodes according to the present invention that includes two uncovered portions of sacrificial gel or other moisture source on the release liner.

FIG. 2 illustrates an embodiment of the present invention that includes two electrode pads 17 and 19 attached to a release liner 15. Leads 21 and 23 extend from each electrode pad. Two sacrificial gel portions 25 and 27 are attached to the release liner.

Figure 3:
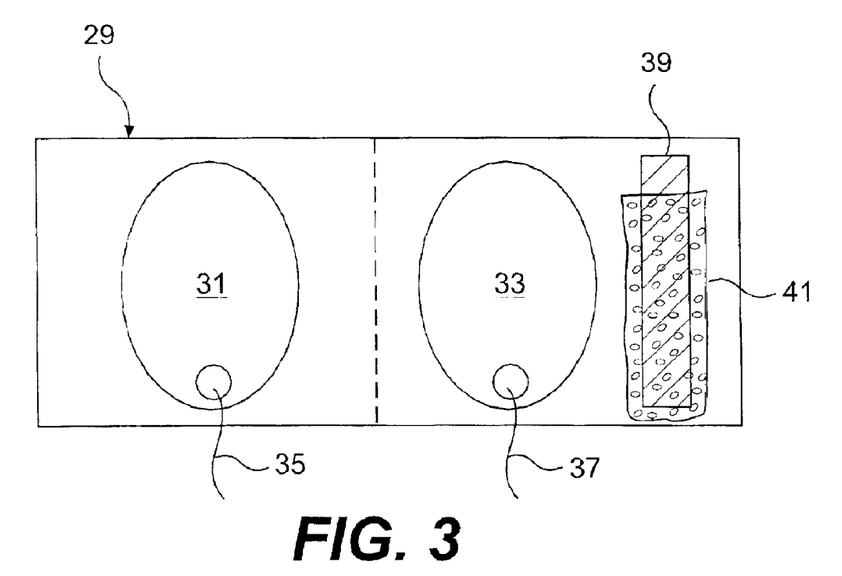
FIG. 3 represents an overhead view of another embodiment of a set of electrodes according to the present invention that includes a partially covered portion of sacrificial gel or other moisture source on the release liner.

FIG. 3 illustrates an embodiment of the present invention that includes two electrode pads 31 and 33 attached to a release liner 29. Leads 35 and 37 extend from each electrode pad. The moisture source 39 in the embodiment shown in FIG. 3 is at lease partially covered by a cover 41 to control release of moisture from the moisture source. The circles on the cover are meant to indicate that the cover is permeable to moisture or includes pores or some other means for moisture to escape from the moisture source.

Figure 4A:
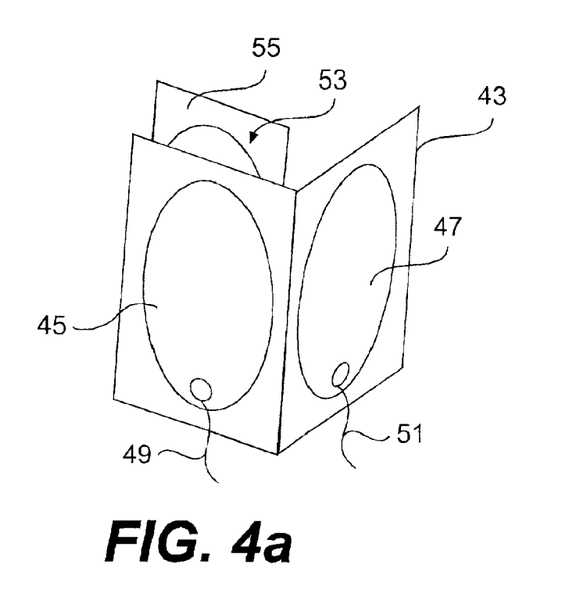
FIGS. 4a and 4b represent perspective views of another embodiment of a set of electrodes according to the present invention that includes at least one sacrificial gel portion or other moisture source on a separate release liner.
Figure 4B:
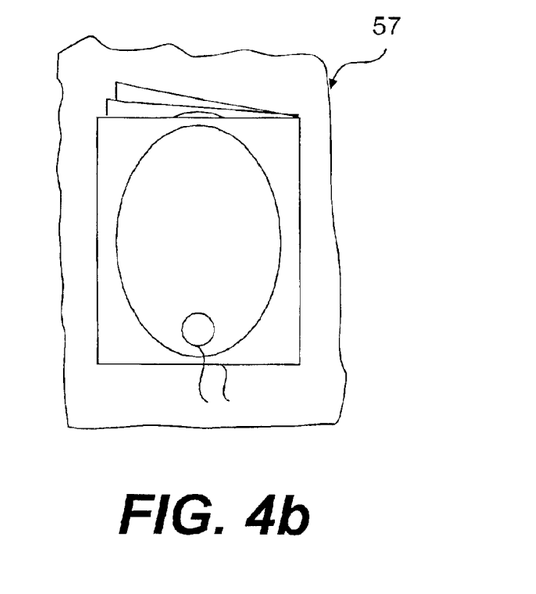

FIG. 4a illustrates an embodiment of the present invention that includes two electrode pads 45 and 47 attached to a release liner 43. Leads 49 and 51 extend from the electrode pads. A sacrificial gel portion 53 is attached to a substrate 55 separate from the release liner 43 that the electrode pads are attached to. The substrate 55 could be a release liner similar to the release liner 43 or could be another material. FIG. 4b illustrates the electrodes, release liner, sacrificial gel and substrate within a package member 57.

Figure 5A:
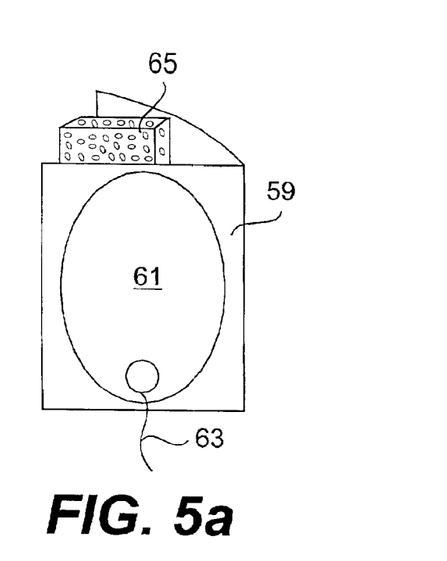
FIGS. 5a and 5b represent perspective views of another embodiment of a set of electrodes according to the present invention that includes at least one moisture source in the form of a moisture-containing sponge.
Figure 5B:
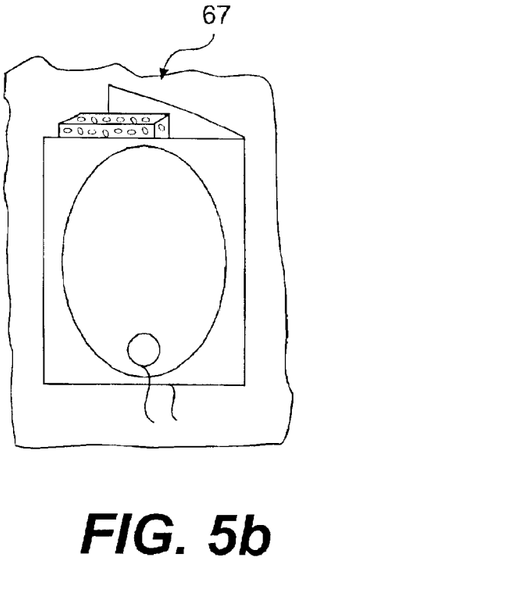

FIG. 5a illustrates an embodiment of the present invention that includes two electrode pads, only one of which, electrode pad 61 is shown, attached to a release liner 59. A lead extends from each electrode pad. FIG. 5a only shows one of the leads 63. The moisture source in the embodiment shown in FIG. 5a is in the form of a moisture-containing sponge 65 separate from the release liner 59 that the electrode pads are attached to. FIG. 4b illustrates the electrodes, release liner, and sponge within a package member 67.

Figure 6:
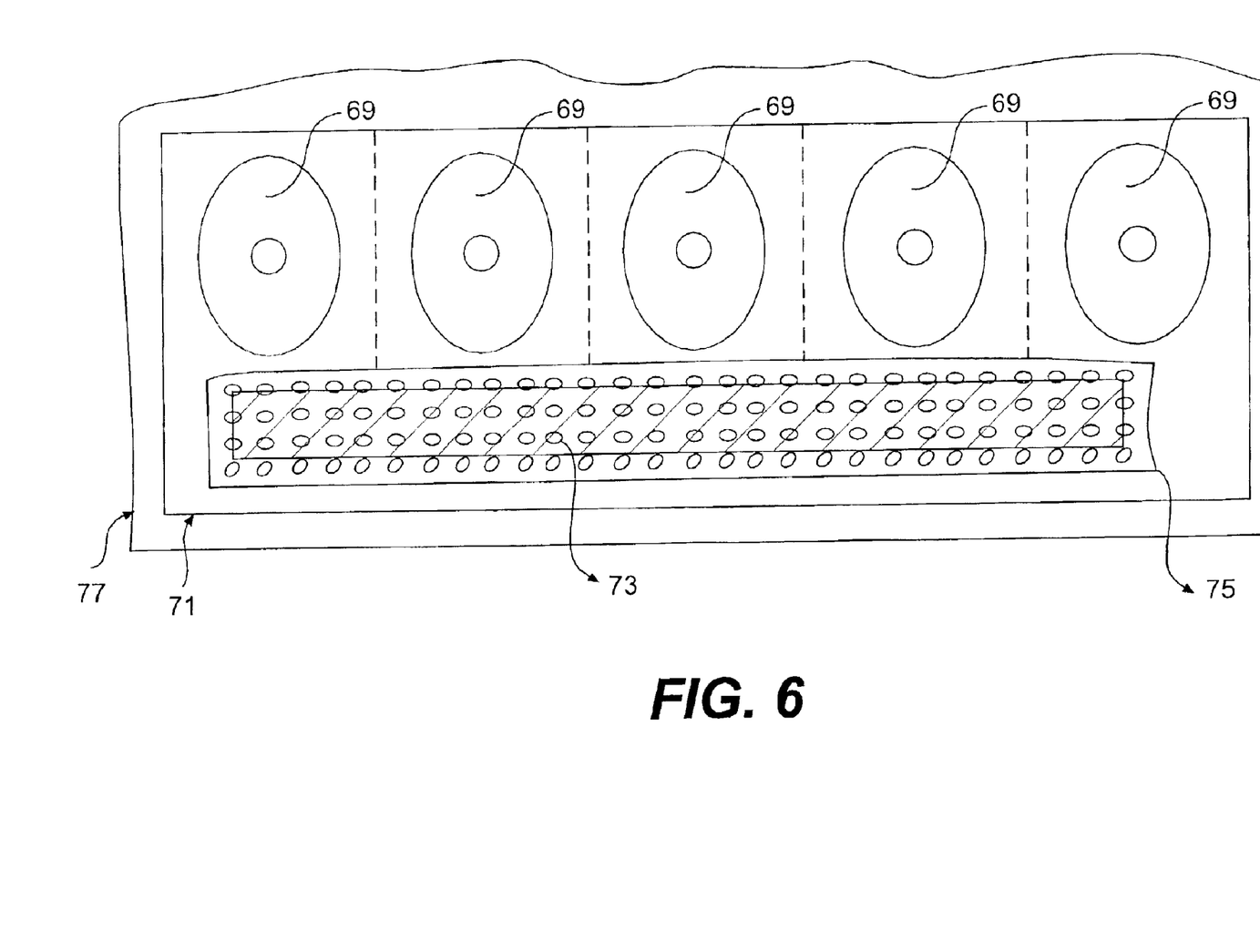
FIG. 6 represents an overhead view of another embodiment of a set of multiple electrodes on a release liner including at least one sacrificial gel portion or other moisture source on the release liner.

FIG. 6 illustrates an embodiment of the present invention that includes a plurality of electrode pads 69 attached to a release liner 71. A sacrificial gel 73 is attached to the release liner 71. The sacrificial gel portion 73 may be covered with a cover 75 if necessary to adjust the rate of moisture transfer from the gel to the package interior. Any cover could be porous or semi-porous. The cover may only cover a portion of the sacrificial gel. Additionally, in the embodiment shown in FIG. 6, as well as any of the embodiments shown in the drawings and described herein, any sacrificial gel, sponge, or any other moisture source could be substituted for any other. The electrodes 69, release liner 71, gel 73 and cover 75 are enclosed within a package member 77.

Figure 7A:
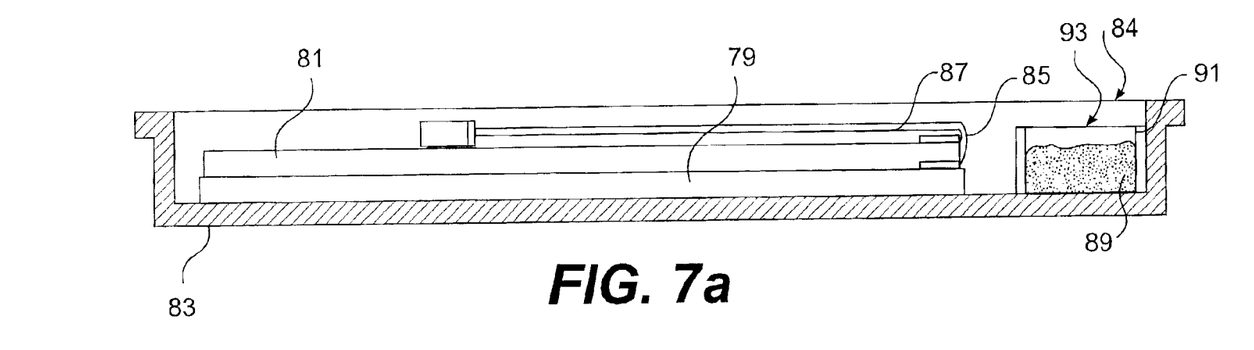
FIGS. 7a and 7b represent, respectively, a cross-sectional and a perspective view of another embodiment of a set of electrodes in a rigid or semi-rigid package including at least one sacrificial gel portion or other moisture source attached to the rigid or semi-rigid portion, or in a well integral to attached to the rigid or semi-rigid portion and including a flexible top cover sealing the electrode pads inside the rigid or semi-rigid portion according to the present invention.
Figure 7B:
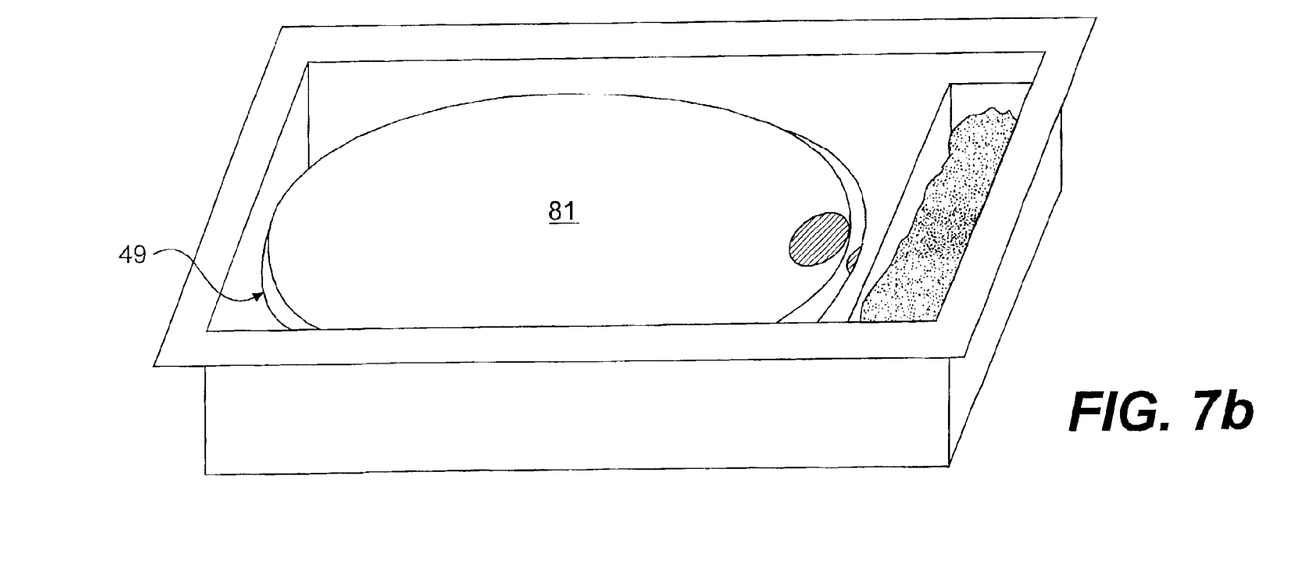

FIG. 7a illustrates an embodiment of the present invention that includes two electrode pads 79 and 81 in a rigid or semi-rigid package member 83. Leads 85 and 87 extend from the electrode pads. A cover 84 may cover the package portion 83 to seal the electrode pads into the package. The cover may be a peelable, flexible cover. FIG. 7b shows a perspective view of the embodiment shown in FIG. 7a.

The moisture source 89 in the embodiment shown in FIG. 7a could include at least one sacrificial gel portion or other moisture source. While the moisture source could be attached to a release liner that the electrode pads are attached to or to a separate substrate, in the embodiment shown in FIG. 7a, the moisture source is arranged in a tray portion 91. The tray portion could be formed as a unitary member with the tray portion that the electrode pads are contained in. Alternatively, the moisture source tray portion could be formed from members attached to the tray portion that the electrodes are arranged in. This is the case with the embodiment shown in FIG. 7a. A cover 93 could at least partially cover the moisture source. The cover may be at least partially permeable to moisture.

Figure 8A:
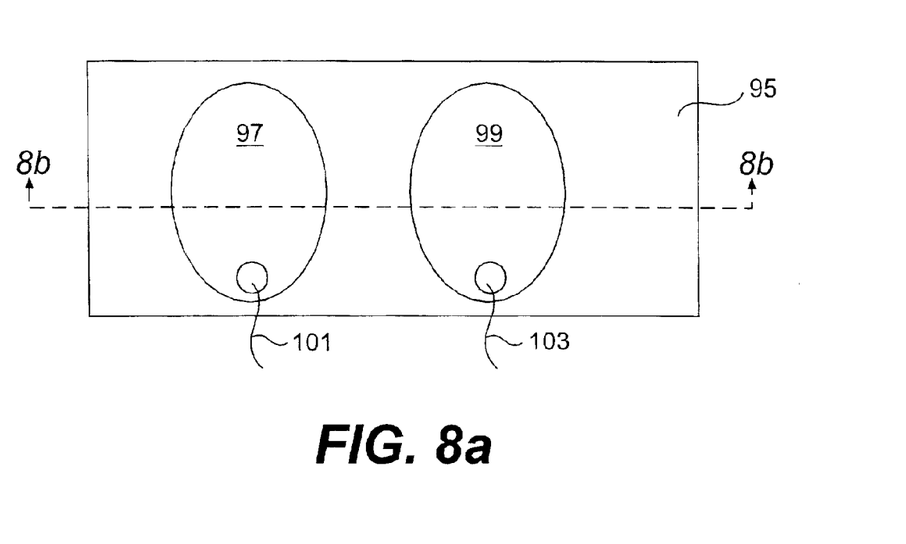
FIGS. 8a and 8b represent, respectively, an overhead and a perspective view of an embodiment of a metal-foil release liner according to the present invention, including two attached electrodes.

FIG. 8a illustrates an embodiment of a release liner 95 according to the present invention. The embodiment of the release liner shown in FIG. 8a includes a metal foil. Two electrodes 97 and 99 are attached to release liner 95. A lead 101 and 103 extends from each electrode pad.

Figure 8B:
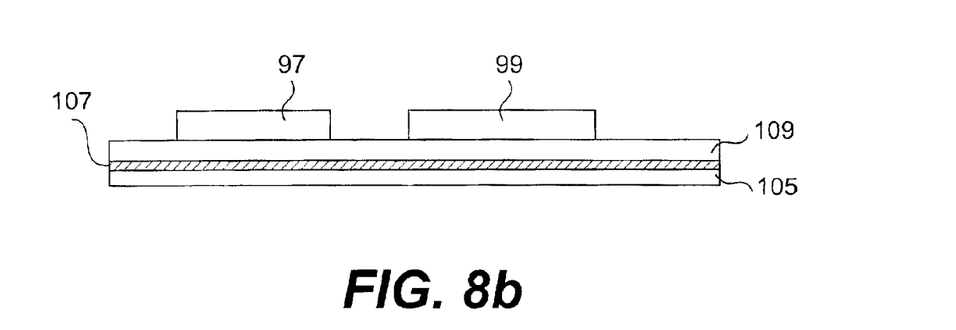

FIG. 8b shows a cross-section of the release liner and electrode pads shown in FIG. 8a, along line 8b–8b in FIG. 8a. The release liner shown in FIG. 8b includes a polymeric layer 105. Polymeric layer 105 could include polypropylene, polyethylene, polyester, and/or any other polymeric material. A conductive layer 107 lies on polymeric layer 103. The conductive layer could include a metal foil. One example of such a metal foil is aluminum foil. Regardless of its composition, the conductive layer could be about 0.00035 inch thick. A release layer 109 lies on the conductive layer. Examples of materials that the release layer could include are silicon-coated polyethylene or polypropylene.

Figure 9A:
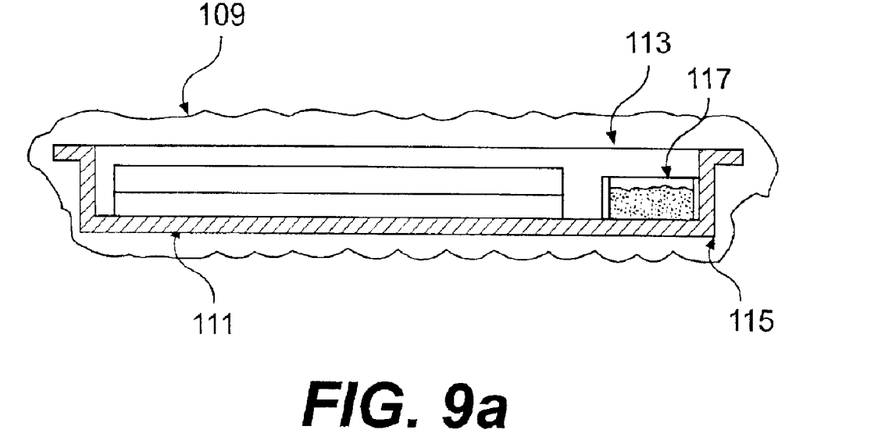
FIG. 9a represents a cross-sectional view of an embodiment a package according to the present invention that includes an inner package portion and an outer package portion with two electrodes and an additional moisture source packaged therein.
Figure 9B:
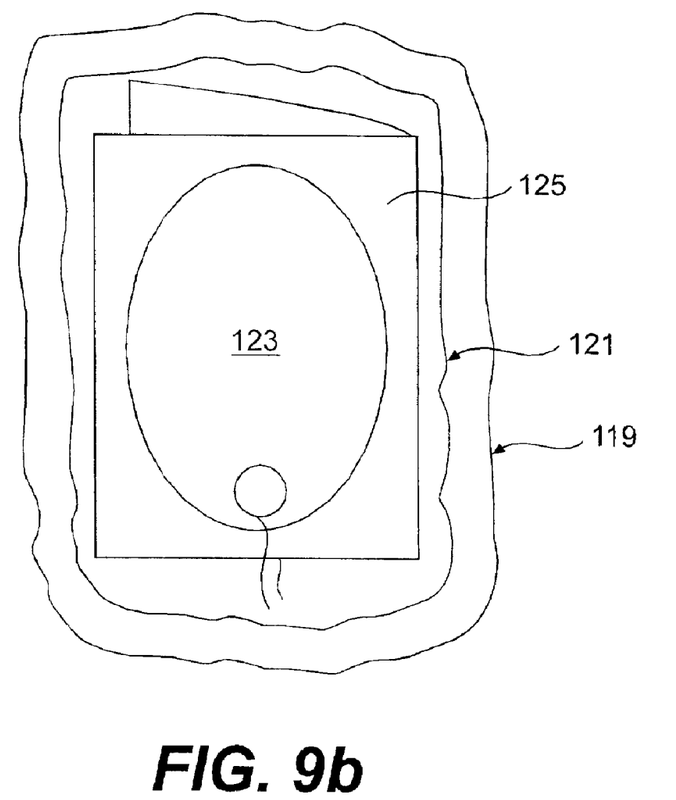
FIG. 9b represents a perspective view of an embodiment of a package according to the present invention that includes an inner package portion and an outer package portion with two electrodes packaged therein.

FIGS. 9a and 9b illustrate embodiments of the present invention that includes a second package portion surrounding a first package portion. Along these lines, FIG. 9a shows the embodiment represented in FIGS. 7a and 7b with a second or outer package 109 around the rigid or semi-rigid package tray portion 111 and cover 113. Although the embodiment shown in FIG. 9a includes additional moisture source 115 with a cover 117, it is optional to include the cover 117 and the moisture source 115. FIG. 9b illustrates an embodiment of a package that includes second package portion 119 surrounding a first package portion 121, which, in turn, encloses electrodes, only one of which, electrode 123 is shown, on release liner 125. The embodiment shown in FIG. 9b does not include an additional moisture source in the package, although it could.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed:

1. A package for increasing shelf life of at least one electrode packaged therein, the package comprising:
   a first package that the electrodes are sealed within, the electrodes comprising an electrode pad comprising a gel; and
   at least one moisture source within an interior surface of the package, which comprises at least one portion of a sacrificial gel that is restrained from movement relative to a position of the electrodes by attachment of the gel and the electrodes to a common liner, and
   wherein the sacrificial gel and the electrode pad gel have a predetermined ratio of moisture content or a predetermined rate of release.

2. The package according to claim 1, wherein the sacrificial gel has a moisture content substantially similar to a moisture content of the gel on the electrodes.

3. The package according to claim 1, wherein the sacrificial gel releases moisture to an interior of the package at a rate similar to the electrode pad gel.

4. The package according to claim 1, further comprising:
   a moisture permeable cover covering at least a portion of an exposed surface of the sacrificial gel.

5. The package according to claim 4, wherein the portion of the sacrificial gel covered is sufficient to result in a rate of moisture release from the gel substantially similar to a rate of moisture release from the electrode pad gel.

6. The package according to claim 1, wherein the sacrificial gel releases moisture to an interior of the package at a greater rate than the electrode pad gel.

7. The package according to claim 1, wherein the sacrificial gel releases moisture to an interior of the package at a slower rate than the electrode pad gel.

8. The package according to claim 1, wherein the package comprises metal foil.

9. The package according to claim 1, wherein the package comprises a rigid or semi-rigid portion with a flexible cover.

10. The package according to claim 1, further comprising:
a cover covering at least a portion of the electrode pad gel.

11. The package according to claim 10, wherein the cover comprises metal foil.

12. The package according to claim 10, further comprising:
   a moisture permeable cover covering at least a portion of an exposed surface of the sacrificial gel, wherein the moisture permeable cover releases moisture to an interior of the package more quickly than the cover on the electrode pad gel.

13. The package according to claim 1, wherein the at least one moisture source comprises at least one of a gel portion, a liquid, and a liquid containing absorbent element.

14. The package according to claim 13, wherein the liquid is water.

15. The package according to claim 13, wherein the absorbent element is a sponge.

16. The package according to claim 1, further comprising: a cover covering at least a portion of the electrode pad gel.

17. The package according to claim 16, wherein the cover comprises metal foil.

18. The package according to claim 16, wherein the cover comprises a polymeric bottom layer adjacent the gel, a metal foil middle layer, and a polymeric top layer.

19. The package according to claim 18, wherein the polymeric bottom layer comprises polyethylene, polypropylene or polyester.

20. The package according to claim 19, wherein the polyethylene is low or high density.

21. The package according to claim 19, wherein the polyethylene, polypropylene or polyester is coated with a low force release surface.

22. The package according to claim 19, wherein the low force release surface comprises silicone.

23. The package according to claim 18, wherein the metal foil is aluminum foil.

24. The package according to claim 17, wherein the top polymeric layer comprises polypropylene, polyethylene or polyester.

25. The package according to claim 19, wherein the polyethylene is low or high density.

26. The package according to claim 1, wherein the package comprises a metal foil pouch.

27. The package according to claim 1, wherein the package comprises package portions.

28. The package according to claim 1, further comprising: an outer package that the first package is sealed within.

29. The package according to claim 1, wherein the electrodes are medical electrodes.

30. The package according to claim 1, wherein the electrodes are defibrillation electrodes.

31. The package according to claim 1, wherein the electrodes are ECG electrodes.

32. A method for increasing shelf life of electrodes comprising at least one gel-containing electrode pad, the method comprising:

sealing at least one moisture source within a package with the electrodes, which includes restraining a sacrificial gel from movement relative to a position of the electrodes within an interior surface of the package by attachment of the gel and the electrodes to a common liner followed by sealing the package, and wherein the sacrificial gel and gel-containing electrode pad have a predetermined ratio of moisture content or a predetermined rate of moisture release.

33. The method according to claim 32, wherein the sacrificial gel has a moisture content substantially similar to the moisture content of the gel of the electrode pads.

34. The method according to claim 32, wherein the sacrificial gel releases moisture, to an interior of the package at a rate similar to the electrode pad gel.

35. The method according to claim 32, further comprising:

covering at least a portion of an exposed surface of the sacrificial gel with a moisture permeable cover.

36. The method according to claim 35, wherein the portion of the sacrificial gel is covered sufficient to result in a rate of moisture release from the gel substantially similar to a rate of moisture release from the gel on the at least one electrode pad.

37. The method according to claim 32, wherein the sacrificial gel releases moisture to an interior of the package at a greater rate than the electrode pad gel.

38. The method according to claim 32, wherein the sacrificial gel releases moisture to an interior of the package at a slower rate than the electrode pad gel.

39. The method according to claim 32, wherein the electrodes and the at least one moisture source are sealed in a package comprising metal foil.

40. The method according to claim 32, wherein the electrodes and the moisture source are sealed in a package comprising a rigid or semi rigid portion and a flexible cover.

41. The method according to claim 32, further comprising: covering at least a portion of the electrode pad gel with a cover.

42. The method according to claim 41, wherein the cover comprises metal foil.

43. The method according to claim 41, further comprising:

covering at least a portion of an exposed surface of the sacrificial gel with a moisture permeable cover, wherein the moisture permeable cover releases moisture to an interior of the package more quickly than the cover on the electrode pad gel.

44. The method according to claim 32, wherein the at least one moisture source comprises at least one of a gel portion, a liquid, and a liquid containing absorbent element.

45. The method according to claim 44, wherein the liquid is water.

46. The method according to claim 44, wherein the absorbent element is a sponge.

47. The method according to claim 32, further comprising: covering at least a portion of the electrode pad gel with a cover.

48. The method according to claim 47, wherein the cover comprises metal foil.

49. The method according to claim 47, wherein the cover comprises a polymeric bottom layer adjacent the gel, a metal foil middle layer, and a polymeric top layer.

50. The method according to claim 49, wherein the polymeric bottom layer comprises polyethylene, polyester or polypropylene.

51. The method according to claim 50, wherein the polyethylene is low or high density.

52. The method according to claim 50, wherein the polyethylene, polyester or polypropylene is coated with a low force release surface.

53. The method according to claim 50, wherein the low force release surface comprises silicone.

54. The method according to claim 49, wherein the metal foil is aluminum foil.

55. The method according to claim 49, wherein the top polymeric layer comprises polypropylene, polyester or polyethylene.

56. The method according to claim 50, wherein the polyethylene is low or high density.

57. The method according to claim 32, wherein the package comprises a metal foil pouch.

58. The method according to claim 32, further comprising:

sealing the electrodes in two package pieces.

59. The method according to claim 32, further comprising:

sealing the first package in an outer package.

* * * * *